United States Patent [19]

Gandolfi et al.

[11] Patent Number: 4,918,087
[45] Date of Patent: Apr. 17, 1990

[54] 2-THIOMETHYL-SUBSTITUTED-PYRIDINE AND -3,5-DICARBOXYLATES HAVING ANTI-HYPERTENSIVE ACTIVITY

[75] Inventors: Carmelo A. Gandolfi; Marco Frigerio; Odoardo Tofanetti; Sergio Tognella, all of Milan, Italy

[73] Assignee: Boehringer Biochemia Robin S.P.A., Milan, Italy

[21] Appl. No.: 167,164

[22] Filed: Mar. 11, 1988

[30] Foreign Application Priority Data

Mar. 13, 1987 [IT] Italy ................. 19800 A/87

[51] Int. Cl.⁴ ................. C07D 213/55; C07D 213/56; A61K 31/44
[52] U.S. Cl. ................. 514/356; 546/286; 546/305; 546/309; 546/316; 546/321
[58] Field of Search ................. 546/321; 514/277, 356

[56] References Cited

U.S. PATENT DOCUMENTS 4,845,113 7/1989 Gandolfi et al. ................. 514/356

Primary Examiner—Alan L. Rotman
Attorney, Agent, or Firm—Armstrong, Nikaido, Marmelstein, Kubovcik & Murray

[57] ABSTRACT

Pyridines of formula I

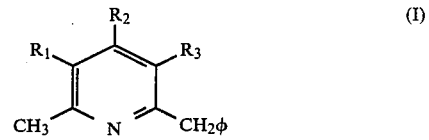

wherein $R_1$ is acetyl, benzoyl, cyano, nitro, alkoxycarbonyl or aminocarbonyl groups; $R_2$ is an optionally substituted aryl or a heterocyclic group; and $\phi$ is a sulphurated residue such as alkylthio, cycloakylthio, arylthio, heteroarylthio, aminoalkylthio.

Compounds I are useful in therapy in cardiovascular field.

5 Claims, No Drawings

2-THIOMETHYL-SUBSTITUTED-PYRIDINE AND -3,5-DICARBOXYLATES HAVING ANTI-HYPERTENSIVE ACTIVITY

The present invention refers to 2-thiomethyl-substituted pyridines, a method for their preparation and pharmaceutical compositions containing them.

The compounds of the invention have the following formula I

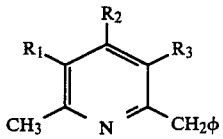

wherein:

$R_1$ is acetyl, benzoyl, cyano, nitro, a $CO_2R_5$ or a $CONR_6R_7$ group;

$R_2$ is a phenyl ring, unsubstituted or substituted by one or more $C_1-C_6$-alkyl, $C_1-C_6$-alkoxy, halo-$C_1-C_4$-alkoxy, halo-$C_1-C_6$-alkyl, halogen, nitro, cyano, $C_1-C_6$-alkoxycarbonyl, $C_1-C_6$-alkylthio, $C_1-C_6$-alkylsulphinyl; pentafluorophenyl: α or β-napthyl; a 5 or 6 membered heterocyclic ring; α-benzo-[2,3-b]-1,4-dioxan-α-yl; α-benzofuroxanyl;

$R_3$ is a $CO_2R_5$ group;

φ is selected in the group of:

(a) a thiol group free or esterified with a fatty $C_1-C_{12}$-acid;

(b) a thiouronium salt of formula $-S-C(=NR_8)NR_9R_{10}^{(+)}$ $Y^{(-)}$ wherein $Y^{(-)}$ is a pharmaceutically acceptable anion and $R_8$, $R_9$, $R_{10}$ that can be the same or different, are hydrogen or $C_1-C_4$-alkyl group;

(c) a thioether $-S(O)_n-R_4$ residue wherein n is 0, 1 or 2 and $R_4$ is selected in the group consisting of:

(a') $C_1-C_5$-alkyl, $C_3-C_5$-alkeynyl groups or unsubstituted $C_3-C_5$-alkinyl groups;

(b') a $C_3-C_7$-cycloaliphatic residue;

(c') an aryl group, optionally substituted by one or more halogen, hydroxy, nitro, cyano, acetyl, $C_1-C_6$-alkyl, halo-$C_1-C_6$-alkyl, amino, monoalkylamino, dialkylamino, carboxy, $C_1-C_4$-alkoxycarbonyl, imidazol-1-yl, $C_1-C_3$-alkoxy, $C_1-C_3$-alkylthio or $C_1-C_{12}$ acylamino groups;

(d') a 5 or 6-membered saturated or unsaturated heterocyclic ring containing at least one heteroatom selected from N, O, S, unsubstituted or substituted by one or more halogen, $C_1-C_6$-alkyl, $C_1-C_6$-alkoxy, halo-$C_1-C_6$-alkyl, monoalkylamino, dialkylamino, cyano, carboxy, $C_1-C_4$-alkoxycarbonyl, $-CONR_6R_7$, aryloxyalkyl or aryl groups;

(e') a mono- or polysubstituted $C_2-C_{12}$ alkyl chain optionally interrupted by one or more oxygen or sulphur atoms wherein the substituents are selected in the group including hydroxy, thio, cyano, halogen, amino, carboxy, $C_1-C_4$-monoalkylamino, di-$C_1-C_4$-alkylamino, $C_1-C_4$-alkoxy, $C_1-C_4$-alkylthio, $C_1-C_4$-acyloxy, $C_1-C_4$-acylthio, $C_1-C_4$-alkoxycarbonyl, $CONR_6R_7$ groups, a $C_3-C_7$-cycloaliphatic residue, an aryl residue, a saturated or unsaturated heterocyclic residue, as above defined;

(f') an oxygenated $C_2-C_{12}$-alkyl chain having formula $-(CH_2)_{n1}-A-(CH_2)_p-B$ wherein A may be an oxyranic cis or trans ring or a masked or unmasked carbonyl moiety and B is hydrogen, $C_1-C_4$-alkyl, cyano, carboxy, $C_1-C_4$-alkoxycarbonyl, $CONR_6R_7$, amino, $C_1-C_4$-monoalkylamino groups; a $C_3-C_7$-cycoaliphatic residue, aryl or saturated or unsaturated 5 or 6 heterocyclic residues, said residues having the above defined meanings;

(g') a group of formula

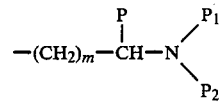

wherein P is hydrogen, $C_1-C_8$-alkyl or a group of formula $-(CH_2)_{p1}-W$; $NP_1P_2$ is a primary, secondary or tertiary amino group, an amido or imido residue wherein $P_1$ and $P_2$ that can be the same or different are hydrogen, $C_1-C_6$-alkyl, $-(CH_2)_{p1}-W$, $C_1-C_6$-acyl groups or an aroyl group; $P_1$ and $P_2$ taken together with the nitrogen atom to which they are bound form a cyclic amide or the residue

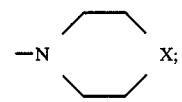

P, when taken together with $P_1$ and the nitrogen atom to which P is bound, may form a pyrrolidine or piperidine ring;

W is hydrogen; methyl; 5 or 6 membered saturated or unsaturated heterocyclic ring containing at least one heteroatom selected a from N, O, S; a $C_3-C_7$-cycloalkyl ring; a phenyl ring unsubstituted or substituted by one or more halogen, nitro, p-imidazol-1-yl, hydroxy, $C_1-C_3$-alkoxy or $CH_2-NP_4P_5$;

X is $-(CH_2)_{p1}$, 0, or N-$P_3$;

$P_3$ is hydrogen, methyl, $C_1-C_3$-acyl, diphenylmethyl, or bis-(4-fluorophenyl)methyl;

$P_4$ and $P_5$, that can be the same or different, are hydrogen, $C_1-C_4$-alkyl or, taken together with the nitrogen atom to which they are bound, form the residue

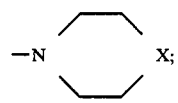

$R_5$ is hydrogen; an ammonium or an alkaline metal cation; a $C_1-C_6$-alkyl group unsubstituted or substituted by hydroxy, amino, $C_1-C_4$-monoalkylamino, di-$C_1-C_4$-alkylamino or $C_1-C_6$-alkoxy groups; $C_3-C_6$-alkenyl; on optionally substituted aryl or a $C_1-C_4$-aralkyl group; each of $R_6$ and $R_7$, that can be the same or different, may be hydrogen, $C_1-C_6$-alkyl, benzyl or aryl;

$n_1$ is an integer from 1 to 6; m is an integer from 1 to 3, p is zero or an integer from 1 to 6 and $p_1$ is zero or an integer from 1 to 3.

The pharmaceutically acceptable salts, optical antipodes, i.e. the single enantiomers; racemic mixtures of optical antipodes, diasteroisomers of compounds I and mixtures of thereof are also included in the scope of the invention.

According to the invention, alkyl, alkenyl, alkoxy and groups may have both a linear or branched chain.

A halo-$C_1$–$C_6$-alkyl group is preferably trihalo-$C_1$–$C_6$-alkyl, particularly trifluoromethyl.

A halo-$C_1$–$C_4$-alkoxy is preferably —$OCHF_2$.

A $C_1$–$C_6$-alkyl group is preferably methyl, ethyl, isopropyl or t-butyl.

A $C_2$–$C_{12}$-alkanoyl group is preferably formyl, acetyl, propionyl, hexanoyl or heptanoyl.

An aroyl group if preferably benzoyl, nicotinoyl or p-aminobenzoyl.

An aryl group is preferably phenyl.

A $C_3$–$C_5$-alkenyl group is preferably allyl.

A $C_3$–$C_5$-alkinyl group is preferably propargyl.

A $C_3$–$C_7$-cycloaliphatic residue is preferably cyclopentyl, cyclohexyl or cycloheptyl.

A $C_1$–$C_4$-monoalkylamino group is preferably a methyl-, ethyl-, isopropyl- or it is benzylamino group.

A di-$C_1$–$C_4$-alkylamino group is preferably a linear group such as dimethyl-, diethyl-, benzyl-methylamino group; or a cyclic group such as pyrrolidin-1-yl, piperidin-1-yl, morpholin-1-yl, 4-methyl-piperazin-1-yl, 4-phenyl-piperazin-1-yl, 4-diphenylmethane-piperazin-1-yl, 4-bis-(p-fluoro-phenyl)methane-piperazin-1yl, 4-ethyl-piperazin-1yl, 4-(2'-hydroxy-ethyl)piperazin-1-yl.

A $C_1$–$C_6$-alkoxycarbonyl is preferably a methoxy, ethoxy or terbutoxy-carbonyl.

A $C_1$–$C_6$-alkoxy is preferably methoxy or isopropoxy.

A $C_1$–$C_6$-alkylthio is preferably methylthio or isopropylthio.

A masked carbonyl function is preferably an acetal of formula

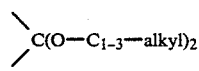

and more preferably a 1,3-dioxolane, a 1,3-dioxane ring wherein one or both the oxygen atoms may be optionally substituted by sulphur atoms. When $R_2$ is a phenyl ring, it is preferably m-nitrophenyl, phenyl, p-fluorophenyl, m-chlorophenyl, o-chlorophenyl, m-cyanophenyl,, o-methylthiophenyl, or m-trifluoromethylphenyl.

When $R_2$ is a heterocyclic ring having 5 or 6 members, it is preferably pyridyl, furanyl or thienyl; when $R_4$ is a heterocyclic ring, it can be either heteromonocyclic or heterobicyclic containing at least one N, S or O atom.

Examples of preferred heteromonocyclic residues are $\alpha$, $\beta$ and $\gamma$-pyridyl, tetrahydrofuryl, thienyl, $\alpha$-pyridyl-N-oxide, 3-hydroxy-$\alpha$-pyridyl, 2 and 4-pyrimidinyl, 1H-1,3,4-triazol-3-yl, 1H-1,2,4-triazol-4-yl, 2-thiazolyl, 1-methyl-tetrazol-5-yl, 2-methyl-1,3,4-thiadiazol-5-yl, 5-amino-1,3,4-thiadiazol-2-yl, 2-amino-1,2,4-triazol-5-yl, 2-hydantoinyl; 2-imidazolinyl, 4-methyl-5-trifuloromethyl-4H-1,2,4-triazolin-3-yl, 1-methyl-imidazol-2-yl, 1-phenyl-1H-tetrazol-5-yl, 4,5-diphenyl-4-oxazolin-2-yl, 5,5-disubstituted-hydantoin-2-yl, 4-phenoxymethyl-5-carboxy-imidazol-2-yl and its esters with lower $C_1$–$C_4$-alcohols, 1H-4,5,6-tetrahydro-pyrimidin-2-yl; 4-substituted-imidazol-2-yl; 5-carboxy-4-substituted-imidazol-2-yl; pyrimidin-2-yl and derivatives thereof with methyl, amino, oxo and/or carboxy groups in positions 4 and 6 of the pyrimidine ring; pyrimidin-4-yl; pyrimidin-6-yl; 2,6-diamino-pyrimidin-4-yl; tetrahydropyran-2-yl; (3,4,5-triacetoxy-6-acetoxymethyl)tetrahydropyran-2-yl; 5-carbomethoxy-4-oxo-pyrimidin-2-yl, 6-propyl-4-hydroxy-pyrimidin-2yl and 6-propyl-4-amino-pyrimidin-2-yl.

Examples of preferred heterobicyclic residues are: 4-(3H)-quinazolin-4-one-2-yl, quinazolinyl-2-; 4-aminopirazol[3,4-d]pyrimidin-2-yl; 6-purinyl; 6,8-dihydroxy-2-purinyl; benzothiazol-2-yl; benzooxazol-2-yl; benzimidazol-2-yl and derivatives thereof substituted in the benzene ring with alkoxy or halogen substituents; quinolin-2-yl, 7-trifluoromethyl-quinolin-4-yl.

The aryl and heterocyclic residue of $R_4$ may be bound to the sulphur atom by means of an alkyl chain, preferably a $C_1$–$C_4$-alkyl chain.

When $R_4$ is a $C_2$–$C_{12}$ mono- or polysubstituted alkyl chain optionally interrupted by one or more oxygen or sulphur atoms, this chain is preferably a residue of $C_2$–$C_{12}$-thiols, such as: 3-phenyl-propan-1-thiol, 3-cyclohexyl-propan-1-thiol, 3-cyclopentyl-propan-1-thiol, 2-propen-1-thiol, 2-propin-1-thiol, 2-mercapto-1-ethanol, and ethers and thioethers thereof such as 2-methoxyethan-1-thiol, 2-ethoxy-ethan-1-thiol, 2-propoxy-ethan-1-thiol, 2-isopropoxy-ethan-1-thiol, 2-pentoxy-ethan-1-thiol, 2-ethylthio-ethan-1-thiol, etc.; 3-mercapto-1,2-propandiol or 1,2-acetals thereof; 2-furyl-methanethiol, 2-(2-furyl)ethan-1-thiol, 2-(2-thienyl)ethan-thiol, 2-(3-thienyl)ethan-1-thiol, 2-(4-methyl-5-thiazol)ethan-1-thiol, 2-(imidazol-1-yl)ethan-1-thiol, 2-($\beta$-pyridyl) ethan-1-thiol, 3-(imidazol-1-yl)propan-1-thiol, 2-($\gamma$-pyridyl)ethan-1-thiol, 2-(pyrrol-1-yl)ethan-1-thiol, 2-(2,5-dimethyl-pyrrol-1-yl)ethan-1-thiol, 3-(2,5-dimethyl-pyrrol-1-yl)-propan-1-thiol; alkylamino-alkylthiols such as 2-dimethylamino-ethan-1-thiol, 2-diethylamino-ethan-1-thiol, 2-butylamino-ethan-1-thiol, 2-N-morpholino-ethan-1-thiol, 2-(N-pyrrolidino)ethan-1-thiol, 2-(N-piperidinyl)ethan-1-thiol, 2-(4'-N-substituted-piperazin-1-yl)-ethan-1-thiol; aminoalkylthiols such as cysteamine, homocysteamine, 4-aminobutan-1-thiol and derivatives thereof wherein the amino group is protected as BOC, acylamide or cyclic amide; 3-amino-, 3-monoalkylamino and 3-dialkylaminopropan-1-thiols, mercaptosacids, i.e. thioglycolic, thiolactic and thiomalic acids and their derivatives such, as esters, amides and nitriles; -aminoacids containing thiol groups such as cysteine, homocysteine and polypeptides obtained starting from these aminoacids such as glutathione;

$R_5$ is preferably methyl, ethyl or isopropyl;

$R_6$, $R_7$, and $R_8$, $R_9$ and $R_{10}$ are preferably hydrogen.

When one of $P_1$ and $P_2$ is an acyl group, it is preferably a $C_1$–$C_4$-acyl, or benzoyl, optionally substituted by amino or methoxy groups.

When $NP_1P_2$ is a cyclic imide, it is preferably obtained starting from succinic, glutaric, maleic, 2,3-diphenylmaleic, phthalic, hexahydro- or tetrahydrophtalic acid.

Particularly preferred compounds of the present invention are those wherein $R_4$ is a group of formula

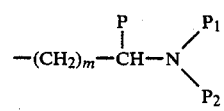

When A is a masked carbonyl function it is preferably 1,3-dioxolane or a dimethoxy- or diethoxyacetal.

The non toxic pharmaceutically acceptable salts include hydrochlorides, hydrobromides, hydroiodides, alkylsulphates, alkyl and arylsulphonates, phosphates, sulphates, maleates, fumarates, succinates, tartrates, citrates as well as other salts normally used in the art.

Salts obtained by variation of the acid employed in some case have special advantages due to an increased stability, increased or lowered solubility, ease of crystallization, absence of disgusting taste, etc., but these are all secondary in comparison to the main physiological action of the free base, that does not depend on the kind of acid used in the preparation of the salt.

Specific examples of preferred compounds of the invention are shown in Table 1:

TABLE I

Structure: pyridine with $H_3C$ and $CH_2\phi$ at 2,6 positions; $R_1$, $R_2$, $R_3$ at 3,4,5 positions.

| $R_1$ | $R_2$ | $R_3$ | $\phi$ |
|---|---|---|---|
| $COOCH_3$ | $m\text{-}NO_2C_6H_4$ | $COOC_2H_5$ | $-S-CH_2CH_2NH_2$ |
| $COOC_2H_5$ | $m\text{-}CF_3C_6H_4$ | $COOC_2H_5$ | $-S-CH_2CH_2NH_2$ |
| $COOC_2H_5$ | $o\text{-}SCH_3C_6H_4$ | $COOC_2H_5$ | $-S-CH_2CH_2NH_2$ |
| $COOCH_3$ | $m\text{-}NO_2C_6H_4$ | $COOC_2H_5$ | $-S-CH_2-CH(CH_3)-NH_2$ |
| $COOC_2H_5$ | $m\text{-}NO_2C_6H_4$ | $COOC_2H_5$ | $-S-CH_2-CH(C_6H_5)-NH_2$ |
| $COOC_2H_5$ | $m\text{-}ClC_6H_4$ | $COOC_2H_5$ | $-S-CH_2CH_2NH-C_3H_7\text{-}i$ |
| $COOCH_3$ | $m\text{-}NO_2C_6H_4$ | $COOCH_3$ | $-S-CH_2CH_2-NH-C_4H_9\text{-}n$ |
| $COOC_3H_7\text{-}i$ | $p\text{-}F-C_6H_4$ | $COOCH_3$ | $-S-CH_2CH_2-NHCH_2-C_6H_5$ |
| $COOCH_2CH_2OCH_3$ | $C_6H_5$ | $COOCH_3$ | $-S-CH_2CH_2-NH-CH_2-$[2-OCH_3, 4-OH, 5-CH_2-morpholino phenyl] |
| $COOMe$ | $m\text{-}NO_2C_6H_4$ | $COOC_2H_5$ | $-S-CH_2CH_2NHCOH$ |
| $COOMe$ | $m\text{-}NO_2C_6H_4$ | $COOC_2H_5$ | $-S-CH_2CH_2NHCOCH_3$ |
| $COOCH_2CH_2N(CH_3)_2$ | $C_6H_5$ | $COOCH_3$ | $S-CH_2CH_2-NHCOC_6H_5$ |
| $COOCH_3$ | $m\text{-}NO_2C_6H_4$ | $COOC_2H_5$ | $S-CH_2CH_2NH_2 \rightarrow O$ |
| $COOCH_3$ | $m\text{-}NO_2C_6H_4$ | $COOC_2H_5$ | $S-CH_2CH_2NH_2 \rightarrow (O)_2$ |
| $COOC_2H_5$ | $o\text{-}Cl-C_6H_4$ | $COOC_2H_5$ | $S-CH_2CH_2NHCOCH_3 \rightarrow O$ |
| $COOC_2H_5$ | $C_6H_5$ | $COOCH_3$ | $S-CH_2CH_2NHCOH \rightarrow (O)_2$ |
| $COOC_2H_5$ | $m\text{-}CNC_6H_4$ | $COOC_3H_7\text{-}i$ | $S-CH_2CH_2NHCOC_6H_5 \rightarrow O$ |
| $CN$ | $m\text{-}NO_2C_6H_4$ | $COOC_2H_5$ | $S-CH_2CH_2NH_2$ |
| $COOEt$ | $C_6H_5$ | $COOC_2H_5$ | $S-C_6H_5$ |
| $COOCH_3$ | $m\text{-}OCH_3C_6H_4$ | $COOC_2H_5$ | $S-CH_2-$(furan-2-yl) |

TABLE I-continued

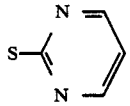

| R₁ | R₂ | R₃ | φ |
|---|---|---|---|
| COOCH₃ | m-NO₂C₆H₄ | COOC₂H₅ | S—COCH₃ |
| COOC₂H₅ | m-NO₂C₆H₄ | COOC₂H₅ | S—CH₂—CH(OH)CH₂OH |
| COOC₂H₅ | m-NO₂C₆H₄ | COOC₂H₅ | 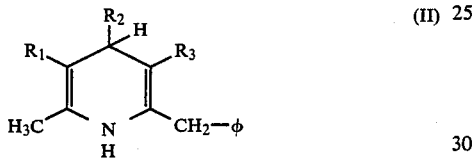 |
| NO₂ | m-NO₂C₆H₄ | COOC₂H₅ | S—CH₂CH₂NH₂ |
| COOCH₃ | C₆H₅ | COOCH₃ | S—CH₂CH₂CN |

The compounds of the invention are obtained by means of a process including:
(a) aromatization of a compound of formula II

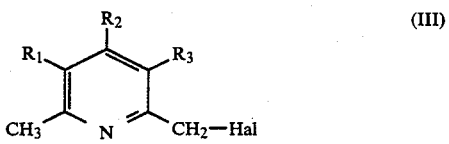     (II)

wherein $R_1$, $R_2$, $R_3$ and $\phi$ are as above defined, to give a compoound of general formula I. The aromatization reaction is carried out by oxidation of a compound II with an oxidizing agent such as potassium or sodium permanganate, nitrous, nitric, chromic acids, palladium on charcoal, sulphur, potassium hexacyanoferrate, chloroanyl or 2,3-dicyano-5,6-dichloroquinone (DDQ). These high potential quinones are preferred oxidizing agents.

The reaction is carried out in an invert solvent; e.g. benzene, toluene, xylene; methanol, ethanol, isopropanol; methylene chloride, chloroform, 1,2-dichloroethane, carbon tetrachloride; acetone, methylethylketone or in mixtures thereof using a slight molar excess of quinone with respect to compounds II, at a temperature ranging from 0° C. to the solvent's reflux temperature, for times ranging from few minutes to 24 hours;

(b) By reaction of a compound of formula III

     (III)

wherein $R_1$, $R_2$, $R_3$ are as above defined and Hal is chlorine, bromine or iodine, with a thiol of formula IV

R'₄SH     (IV)

wherein R'₄ is hydrogen, $C_2$-$C_{12}$-alkanoyl, —C(=NR₈)NR₉R₁₀ or R₄, being R₄, R₈, R₉ and R₁₀ as above defined, thus obtaining a compound of formula I wherein $\phi$ is a thiol or its $C_2$–$C_{12}$ alkanoyl-ester, a thiouronium salt —S—C(N=R₈)NR₉R₁₀(+-)Hal(−) or —S(O)ₙR₄ ($R_4$, $R_8$, $R_9$, $R_{10}$, Hal$^{(-)}$ are as above defined and n is zero) that can optionally be oxidized to give a compound of formula I wherein n is 1 or 2 and, if desired, after removal of known protecting groups optionally present in R₄, converting a compound of formula I, in another compound of formula I and/or if desired, salifying a compound of formula I and/or if desired, obtaining a free compound of formula I from a salt thereof and/or if desired separating a mixture of isomers into the single isomers. The reaction is carried out using equimolecular quantities of a compound III with a compound IV in an inert solvent such as alcohol (for instance methanol, ethanol, isopropanol), an ether (for instance tetrahydrofurane, 1,2-dimethoxyethane, dioxane); a dipolar aprotic solvent (for ex. dimethylsulphoxide, dimethylformamide, 1-methyl-2-pyrrolidinone); aromatic solvents (for ex. benzene, toluene, pyridine), chlorinated solvents (for ex. methylene chloride, 1,2-dichloroethane) and mixtures thereof, in the presence of an equimolecular quantity or an excess of a base selected in the group of NaOH, K₂CO₃, Na₂CO₃, LiCO₃, KHCO₃, MeONa, EtONa, T-BuOK, (EtO)₂Mg, CaH₂, NaH, NaNH₂, isopropylamine, triethylamine, N-methyl-piperidine, 4-dimethylamino-pyridine, etc., at a temperature ranging from −30° C. to the solvent's reflux temperature, for reaction periods ranging from a few minutes to 48 hours.

When R'₄ is —C(=NR₈)NR₉R₁₀ the reaction is carried out in the above specified conditions, but preferably in the absence of a base, at a temperature ranging from the room temperature to the solvent's reflux temperature, for times ranging from 1 to 48 hours.

Compounds of formula II, are claimed and described in P.C.T. Application No. EP 86/00445 of 29.7.1986 in the Applicant's name: the compounds of formula III are obtained starting from their 1,4-dihydropyridine analogues of formula V described in EP-A-0212340 in Applicant's name

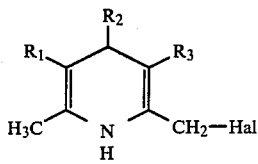

(V)

submitting these halo-methyl compounds to the aromatizat process above described in the conversion of a compound of formula II in a compound of formula I. The thiols of formula IV are known compounds or are prepared according to P.C.T. Applicant N. EP 86/00445.

The compounds of the invention show a long lasting antihypertensive effect when administered by oral route to spontaneously hypertensive rats.

The antihypertensive effect has a slow onset and the decrease of the mean blood pressure is reached 4–6 hours after the administration; for ex. 3-carboethoxy-5-carbomethoxy-4-(m-nitrophenyl)-6-methyl-pyridine derivatives:

2-aminoethylthiomethyl
2-aminoethylsulphinylmethyl
2-aminoethylsulphonylmethyl induce a lowering of mean blood pressure of 10–20% when administered by the oral route at dosages of 3 mg/kg.

The compounds of the invention show moreover a low acute toxicity when administered to rats by the oral and intraperitoneal route.

The clear antihypertensive effect of the compounds of the invention is not due or related to putative $Ca^{++}$ antagonist properties: infact compounds I are totally unable to inhibit calcium induced contraction of K-depolarized rat aorta and do not displace or reduce binding of 3H-nitrendipine from $Ca^{++}$ antagonist receptor.

Due to their particular pharmacological characteristics, the compounds of the invention are useful in human therapy for treating cardiovascular pathologies, particularly hypertensive forms. In order to achieve the desired effects in human and veterinary therapy, the compounds may be administered by parenteral route (by intravenous, hypodermic or intramuscular injections) infusional, rectal or oral route. The compounds may be administered to the patient in pure form or formulated into pharmaceutical compositions.

Suitable pharmaceutical compositions may be prepared in accordance with known techniques, such as described for example in "Remington's Pharmaceutical Sciences Handbook", Hack Publishing Co., U.S.A.

When the compounds of the invention are used as antihypertensives, the dosage will vary according to the seriousness of hypertension and administration route.

The amount of active principle administered by the oral route may range from $1\gamma/Kg/die$ to 1 mg/Kg/die and preferably from $5\gamma/mg/Kg/die$ to 0.1 mg/Kg/die.

The amount of active principle administered by the parenteral route may vary from $0.1\gamma/Kg/die$ to 0.5 mg/Kg/die, preferably from $0.5\gamma/Kg/die$ to 0.2 mg/Kg/die.

A unit dose may contain, for instance, from $50\gamma$ to 70 mg of active principle.

The compounds of the invention may be administered even once a day, but more spaced and/or repeated administrations may be convenient at least in some cases and may vary according to the patient's conditions and to the administration route and dosage. In the present case the word "patient" means hot-blooded animal, man included.

For the oral administration the compounds may be given in solid or liquid preparations, in form of capsules, pills, tablets, powders, solutions, suspensions or emulsions. The unit solid dosage can be a hard or soft gelatine capsule, containing lubricants and inert excipients such as lactose, saccharose and starch.

The compounds of the invention may be also formulated into tablets, using conventional excipients such as lactose, saccharose, starch, gelatine, alginic acid, stearic acid, magnesium stearate, etc.

For the parenteral administration, the compounds may be prepared as injectable formulations dissolved or suspended in physiologically acceptable diluents, with a sterile vehicle (water or an oil), with our without addition of other excipients. Oils may be of vegetal, animal or synthetic origin, such as peanut oil, soya or mineral oil. Generally, as a vehicle for injectable solutions, it is possible to use water, aqueous solutions of mineral salts, aqueous solutions of dextrose or other sugars, ethanol, glycols such as propylene or polyethylene glycol.

The compounds may also be administered by the rectal route in form of suppositories, mixtures with conventional vehicles, such as cocoa butter, wax, polyvinylpyrrolidone, polyoxyethylenglycol or derivatives thereof.

The compunds of the invention are preferably administered by the oral route.

The following examples illustrate the invention without limiting it.

Preparation 1

2,3-dicyano-5,6-dichloroquinone (DDQ, 3 g) is added to a chloroform solution (50 ml) of 2-chloromethyl-3,5-dicarboethoxy-4-(m-nitrophenyl)-6-methyl-1,4-dihydropyridine (5 g). After 30 minutes the suspension is filtered on a celite panel, the solvent is evaporated under vacuum, the residue is diluted with ethyl ether (100 ml), washed with water ($2 \times 20$ ml), with a NaHCO$_3$ saturated solution ($3 \times 10$ ml) and water ($3 \times 10$ ml), dried on Na$_2$SO$_4$ and the ether is evaporated under vacuum. The residue is filtered on a silica gel column (30 g, eluent 1,2-dichloroethane), the solvent is evaporated under vacuum and the residue is crystallized from isopropyl alcohol.

3,5 g of 2-chloromethyl-3,5-dicarboethoxy-4-(m-nitrophenyl)-6-methylpyridine, m.p. 76°–78° C. are obtained.

In the same way the following compounds were prepared:

2-chloromethyl-3-carboethoxy-5-carbomethoxy-4-(m-nitrophenyl)-6-methylpyridine, m.p. 93°–94° C.;
2-chloromethyl-3-carboethoxy-5-cyano-4-(m-nitrophenyl)-6-methylpyridine;
2-chloromethyl-3,5-dicarboethoxy-4-(m-trifluoromethylphenyl)-6-methylpyridine;
2-chloromethyl-3,5-dicarboethoxy-4-(o-methylthiophenyl)-6-methylpyridine;
2-chloromethyl-3,5-dicarboethoxy-4-(m-chlorophenyl)-6-methylpyridine;
2-chloromethyl-3-carboethoxy-5-carbomethoxy-4)m-methoxyphenyl)-6-methylpiridine.

EXAMPLE 1

DDQ (0, 25 g) is added at room temperature to a chloroform solution (4, 5 ml) of 2-(2-formanidoethylthio) methyl-3-carboethoxy-5-carbomethoxy-4-(m-nitrophenyl)-6-methyl-1,4-dihydropyridine (0, 43 g) (this product having a m.p. 109°–111° C., obtained according to P.C.T. EP 86/00445).

After 15 minutes it is filtered on celite, the chloroform is evaporated under vacuum, the residue is dissolved in ethyl acetate (10 ml), the organic phase is washed with NaOH (0.3N; 4×5 ml) and with water (3×10 ml, dried ($Na_2SO_4$) and evaporated under vacuum.

400 mg of 2-(2-formamidoethylthio)methyl-3-carboethoxy-5-carbomethoxy-4-(m-nitrophenyl)-6-methylpyridine are obtained as an amorphous solid.

$^1$H-NMR ($CDCl_3$) δ (TMS): 0.8–1.1 (3H, t); 2.5–2.9 (5H; s+m); 3.1–3.7 (5H; s+m); 3.8–4.20 (4H, m); 6.0–6.8 (1H, m); 7.1–8.2 (5H, m).

Likewise, for oxidation with DDQ of a 2-(2-acetamidoethylthio)-methyl-3-carboethoxy-5-carbomethoxy-4-(m-nitrophenyl)-6-methyl-1,4-dihydropyridine, 2-(2-formamidoethylthio)-methyl-3-carbomethoxy-5-carbomethoxy-4-(2-methylthiophenyl)-6-methyl-1,4-dihydropyridine, 2-(2-benzamidoethylthio)-methyl-3,5-dicarboethoxy-4-(m-chlorophenyl)-6-methyl-1,4-dihydropyridine, 2-(phenylthio)methyl-3,5-dicarboethoxy-4-phenyl-6-methyl-1,4-dihydropyridine, 2-(2-furylmethylthio)methyl-3-carboethoxy-5-carbomethoxy-4-(m-methoxyphenyl)-6-methyl-1,4-dihydropyridine, the following 6-methylpyridines were obtained:

2-(2-formamidoethylthio)methyl-3-carboethoxy-5-carbomethoxy-4-(m-nitrophenyl);

2-(2-formamidoethylthio)methyl-3-carboethoxy-5-carbomethoxy-4-(2-methylthiophenyl)-; amorphous solid $^1$H-NMR ($CDCl_3$) δ (TMS): 1.0–1.3 (3H, t); 2.10–3 (8H, s+s+m); 3.1–3.7 (5H; s+m); 3.8–4.2 (4H, m); 6.5–6.8 (1H, m); 6.9–7.5 (4H, m); 8.1 (1H, s).

2-(2-benzamidoethylthio)methyl-3,5-dicarboethoxy-4-(m-chlorophenyl).

2-(phenylthio)methyl-3,5-dicarboethoxy-4-phenyl.

2-(2-furylmethylthio)methyl-3-carboethoxy-5-carbomethoxy-4-(m-methoxyphenyl).

EXAMPLE 2

A solution of 2-chloromethyl-3-carboethoxy-5-carbomethoxy-4-(m-nitrophenyl)-6-methylpyridine (8.5 g) in ethan (20 ml) is added dropwise to a solution at −10° C. of cysteamine hydrochloride (1.6 g) and NaOH (solution 20% p/p; ml 7.3) in ethanol (50 ml).

After 15 minutes the solution is warmed to room temperature, acidified with acetic acid (final pH 3.5–4) and evaporated to a small volume. The residue is partitioned between water (100 ml) and ethyl ether (50 ml), the ether phase is eliminated, the aqueous phase is made basic with a $NaHCO_3$ saturated solution and extracted with ethyl ether (3×50 ml).

The organic phase is dried on $Na_2SO_4$, then it is evaporated under vacuum to give 9 g of an oil.

A solution of fumaric acid (2.5 g) in ethanol (25 ml) is added dropwise to a solution, kept at reflux, of the above oil (9 g) in ethyl acetate (180 ml). The suspension is refluxed for 30 minutes, then it is cooled at room temperature, stirred for one hour, the solid is filtered, and dried at 50° C. under vacuum.

8.5 g of 2-(2-aminoethylthio)-methyl-3-carboethoxy-5-carbomethoxy-4-(m-nitrophenyl)-6-methylpyridine fumarate $C_{20}H_{23}N_3O_6S\cdot C_4H_4O_4$, m.p. 145°–147° C., are obtained.

Using in the conditions above described a thiol selected in the group of cysteamine, 2-amino-2-methylethanthiol, 2-amino-2-phenylethanthiol, 2-N-isopropylamino-ethanthiol, 2-N-butylaminoethanthiol and 2-N-benzylaminoethanthiol and a pyridine selected in the group of 2-chloromethyl-3,5-dicarboethoxy-4-(m-trifluoro methyl-phenyl)-6-methylpyridine, 2-chloromethyl-3,5-dicarboethoxy-4-(o-methylthiophenyl)-6-methylpyridine, 2-chloromethyl-3-carboethoxy-5-carbomethoxy-4-(m-nitrophenyl)-6-methylpyridine, 2-chloromethyl-3,5-dicarboethoxy-4-(m-chlorophenyl)-6-methylpyridine, 2-chloromethyl-3,5-dicarbomethoxy-4-(m-nitrophenyl)-6-methylpyridine and 2-chloromethyl-3-carbomethoxy-5-carboisopropoxy-4-(p-fluorophenyl)-6-methylpyridine, the following compounds were obtained:

2-(2-aminoethylthio)-methyl-3,5-dicarboethoxy-4-(m-trifluoromethylphenyl)-6-methylpyridine;

2-(2-aminoethylthio)-methyl-3,5-dicarboethoxy-4-(o-methylthiophenyl)-6-methylpyridine;

2-(2-aminopropylthio)-methyl-3-carboethoxy-5-carbomethoxy-4-(m-nitrophenyl)-6-methylpyridine;

2-(2-amino-2-phenylethylthio)-methyl-3,5-dicarboethoxy-4-(m-nitrophenyl)-6-methylpyridine;

2-(2-N-isopropylaminoethylthio)-methyl-3,5-dicarboethoxy-4-(m-chlorophenyl)-6-methylpyridine;

2-(2-N-n-butylaminoethylthio)-methyl-3,5-dicarbomethoxy-4-(m-nitrophenyl)-6-methylpyridine;

2-(2-N-benzylaminoethylthio)-methyl-3-carbomethoxy-5-carboisopropoxy-4-(p-fluorophenyl)-6-methylpyridine.

EXAMPLE 3

A solution of m-chloroperbenzoic acid (85%, 1.2 g, one molar equivalent) in 1,2-dichloroethane (13 ml) is dropped in a solution at −10° C. of 2-(2-aminoethylthio)-methyl-3-carboethoxy-5-carbomethoxy-4-(m-nitrophenyl)-6-methylpyridine hydrochloride (2.5 g) in 1,2-dichloroethane (25 ml). The mixture is warmed to 0° C. and the precipitate is filtered (and then eliminated). The organic phase is washed with an $Na_2S_2O_3$ aqueous solution (5%, 2×10 ml) and with water (3×10 ml). The dried organic phase is evaporated on $Na_2SO_4$ and the residue is dissolved in ethyl ether (50 ml). The organic phase is eliminated, the aqueous phase is made basic with a $NaHCO_3$ saturated solution, and extracted with methylene chloride (2×50 ml), dried ($Na_2SO_4$) and evaporated under vacuum.

2 g of 2-(2-aminoethylsulphinyl)-methyl-3-carboethoxy-5-carbomethoxy-4-(m-nitrophenyl)-6-methylpyridine are obtained. Salification with fumaric acid (0.7 g), according to the method described in Example 2, gives 2.6 g of the corresponding fumarate $C_{10}H_{13}N_3O_7S\cdot C_4H_4O_4$, m.p. 170°–172° C.

EXAMPLE 4

A solution of m-chloro-perbenzoic acid (85%, 2.05 g; 2 molar equivalents) in methanol (15 ml) is dropped in a solution at −10° C. of 2-(2-aminoethylthio)methyl-3-carboethoxy-5-carbomethoxy-4-(m-nitrophenyl)-6-methylpyridine fumarate (2.85 g) in methanol (28 ml). The solution is warmed at +15° C. stirred for 30′, then the solvent is evaporated at reduced pressure, (paying attention that the warming bath does not exceed 35° C.).

The residue is dissolved in methylene chloride and treated as described in the Example 3.

1.83 g of 2-(2-aminoethylsulphonyl)-methyl-3-carboethoxy-5-carbomethoxy-4-(m-nitrophenyl)-6-methypyridine fumarate are obtained $C_{20}H_{24}N_3O_8S \cdot C_4H_4O_4$, m.p. 157°–158° C.

We claim:

1. A compound of formula I

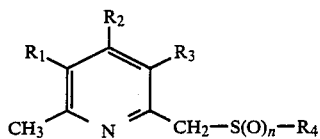

wherein:

$R_1$ is $COOR_5$;

$R_2$ is selected from the group consisting of m-nitrophenyl and m-cyanophenyl;

$R_3$ is $COOR_5$;

$R_5$ is a $C_{1-6}$ alkyl group;

n is zero; and $R_4$ is a group of formula

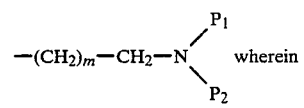

m is an integer from 1 to 3, $P_1$ and $P_2$ are both hydrogen, or one of $P_1$ or $P_2$ is hydrogen and the other is selected from the group consisting of a $C_{1-6}$ alkyl group and benzyl;

or a pharmaceutically acceptable salt thereof.

2. A compound according to claim 1, wherein said compound is 2-(2-aminoethylthio)-methyl-3-carboethoxy-5-carbomethoxy-4-(m-nitrophenyl)-6-methylpyridine.

3. A compound according to claim 1, wherein $R_5$ is a $C_{1-3}$ alkyl group.

4. A method for treating hypertension comprising administering to a subject having hypertension an anti-hypertension effective amount of the compound of any one of claims 2, 1 or 3.

5. A composition for the treatment of hypertension, comprising an inert carrier and an anti-hypertension effective amount of the compound of any one of claims 2, 1 or 3.

* * * * *

UNITED STATES PATENT AND TRADEMARK OFFICE
CERTIFICATE OF CORRECTION

PATENT NO. : 4,918,087
DATED : April 17, 1990
INVENTOR(S) : GANDOLFI et al

It is certified that error appears in the above-identified patent and that said Letters Patent is hereby corrected as shown below:

On the cover page, Item [30], "19800 A/87" should read
--19700 A/87--.

Signed and Sealed this

First Day of October, 1991

Attest:

HARRY F. MANBECK, JR.

*Attesting Officer*   Commissioner of Patents and Trademarks